United States Patent [19]

Lorenz

[11] 4,021,437

[45] May 3, 1977

[54] 6-ETHYLAMINO-2-PICOLINE FROM 6-ACETAMIDO-2-PICOLINE

[75] Inventor: Roman R. Lorenz, Rensselaer County, N.Y.

[73] Assignee: Sterling Drug Inc., New York, N.Y.

[22] Filed: Mar. 15, 1976

[21] Appl. No.: 667,136

[52] U.S. Cl. .................... 260/296 R; 260/295 AM
[51] Int. Cl.$^2$ ...................................... C07D 213/24
[58] Field of Search ............................... 260/296 R

[56] References Cited

UNITED STATES PATENTS 2,894,822  7/1959  MacWood .......................... 423/294

FOREIGN PATENTS OR APPLICATIONS 50-100064  8/1975  Japan ............................. 260/296 R

OTHER PUBLICATIONS

Papanastassiou et al., J. Org. Chem. vol. 29, pp. 2870 to 2872 (1964).

*Primary Examiner*—John D. Randolph
*Attorney, Agent, or Firm*—Robert K. Bair; B. Woodrow Wyatt

[57] ABSTRACT

Improvements in the reduction of 6-acetamido-2-picoline to produce 6-ethylamino-2-picoline, the improvements being in the use of diborane as the reducing agent and in the use of a low boiling petroleum solvent to separate the soluble 6-ethylamino-2-picoline from the insoluble starting material 6-acetamido-2-picoline. The 6-ethylamino-2-picoline final product is useful as an intermediate in a known method of preparing nalidixic acid, an antibacterial agent.

14 Claims, No Drawings

6-ETHYLAMINO-2-PICOLINE FROM 6-ACETAMIDO-2-PICOLINE

BACKGROUND OF THE INVENTION

1. Field of the Invention

This invention relates to a process for preparing and purifying 6-ethylamino-2-picoline, an intermediate for a method of synthesizing nalidixic acid.

2. Description of the Prior Art

The various known methods of preparing 6-ethylamino-2-picoline usually result in the production of the desired compound together with some starting material, e.g., 6-amino-2-picoline or 6-acetamido-2-picoline, and/or one or more by-products, e.g., 6-diethylamino-2-picoline, ring-hydrogenated by-products using certain reducing agents such as lithium aluminum hydride and sodium borohydride. Separation of the desired 6-ethylamino-2-picoline from the starting material and/or by-product(s) is effected by various means, e.g., vacuum distillation, selective recrystallization, selective reaction of the starting material or by-product with an appropriate reagent and separation of the resulting derivative, and the like.

The Koei Japanese Patent Publication No. 15269/74, published Apr. 13, 1974, which was based on Application No. 16282/71, filed Mar. 20, 1971, describes a process for producing 6-ethylamino-2-picoline, characterized by catalytically hydrogenating 6-amino-2-picoline in liquid phase in the presence of an excess of acetaldehyde. By-product 6-diethylamino-2-picoline is removed by fractional distillation under high vacuum.

The Mitsubischi Chemical Industries, Ltd. provisional Japanese Patent Publication No. SHO49-108080, published Oct. 14, 1974 and based on Application No. SHO48-21945, filed Feb. 23, 1973, describes a process for the purification of 6-ethylamino-2-picoline by heating 6-1-ethyl-amino-2-picoline containing starting material 6-amino-2-picoline with an orthoformate in the presence of a weak acidic catalyst and separating by distillation the unreacted 6-ethylamino-2-picoline from the reaction products of 6-amino-2-picoline and an orthoformate, namely, N,N'-bis(6-methyl-2-pyridine)formamide or alkyl (6-methyl-2-pyridyl)-formimidate.

The Kohjin Co., Ltd., Japanese Provisional Patent Publication No. 50-100064/75, published Aug. 8, 1975 and based on Application No. 49-6071/74, filed Jan. 11, 1974, discloses that the starting material, 6-ethylamino-2-picoline, used for the invention described therein can be prepared by reducing 6-acetamido-2-picoline with lithium aluminum hydride. No experimental details are given in this Kohjin patent publication for preparing 6-ethylamino-2-picoline, but it appears that the reduction of 6-acetamido-2-picoline with lithium aluminum hydride most likely would produce a mixture of the final product, some starting material, and probably one or more ring-hydrogenated by-product(s).

The Koei Chemical Co., Ltd., British patent specification No. 1,338,023, published Nov. 21, 1973, shows in Example 2 the use of "6-methyl-2-ethylaminopyridine" (same as 6-ethylamino-2-picoline) as an intermediate in preparation of nalidixic acid.

SUMMARY OF THE INVENTION

The invention relates to improvements in the reduction of 6-acetamido-2-picoline to produce 6-ethylamino-2-picoline, the improvements being in the use of diborane as the reducing agent and the use of a low boiling petroleum solvent to separate the soluble 6-ethylamino-2-picoline from the insoluble starting 6-acetamido-2-picoline.

DETAILED DESCRIPTION INCLUSIVE OF PREFERRED EMBODIMENTS

In a process for producing 6-ethylamino-2-picoline by reduction of 6-acetamido-2-picoline, the invention resides in the improvement comprising carrying out the reduction using diborane as the reducing agent. In a preferred embodiment, the reduction is carried out using tetrahydrofuran as a solvent.

In a process for producing 6-ethylamino-2-picoline by reduction of 6-acetamido-2-picoline, the invention also resides in the improvement comprising using a low boiling petroleum solvent to separate the soluble 6-ethylamino-2-picoline from the insoluble 6-acetamido-2-picoline. In a preferred embodiment, the low boiling petroleum solvent is n-hexane.

The invention in an another process aspect comprises the combination of said improvements comprising carrying out the reduction using diborane as a reducing agent and using a low boiling petroleum solvent to separate the soluble 6-ethylamino-2-picoline from the insoluble 6-acetamido-2-picoline. In a preferred embodiment, the reduction is carried out using tetrahydrofuran as a solvent and the low boiling petroleum solvent is n-hexane.

The term, "a low boiling petroleum solvent" as used herein, preferably means an alkane having 5, 6 or 7 carbon atoms or mixtures thereof having a boiling point of about 28° through 100° C., a preferred low boiling petroleum or alkane solvent being n-hexane having a boiling point of 65°–69.4° C.

The manner of making and using the instant invention will now be generally described so as to enable a person skilled in the art of chemistry to make and use the same, as follows:

The reduction of 6-acetamido-2-picoline with diborane to produce 6-ethylamino-2-picoline is conveniently carried out by mixing the reactants, preferably in a solution in an inert non-polar solvent at about 0° to 70° C. until the reaction is completed. In practicing the invention I found it convenient to use tetrahydrofuran as the solvent and to mix the reactants at about 0° C., preferably under an inert atmosphere, e.g., nitrogen, and then to allow the reaction mixture, preferably with stirring, to warm up to room temperature (about 25°–30° C.) and then slowly bringing the reaction mixture to reflux and holding it at reflux until completion of the reaction. Other inert non-polar solvents can be used, e.g., ethylene glycol dimethyl ether, and the like. Preferably the reaction mixture was then first made strongly acidic with an aqueous mineral acid, e.g., hydrochloric acid, and then the resulting acidic solution was made basic by addition of aqueous alkali hydroxide solution, potassium or sodium hydroxide, followed by filtering the alkaline mixture and concentrating the filtrate in vacuo. The remaining residue containing the desired 6-ethylamino-2-picoline together with some starting material, 6-acetamido-2-picoline, was shaken well with a low boiling petroleum or alkane solvent, preferably n-hexane, b.p. 65°–69.4° C., and the insoluble 6-acetamido-2-picoline was filtered off. The alkane filtrate was first optionally washed with aqueous alkali hydroxide solution and once with brine, and then it was concentrated in vacuo to remove the alkane and to produce the desired 6-ethylamino-2-picoline. The remaining 6-ethylamino-2-picoline after removal of alkane can be further purified by distillation under vacuum to yield a highly purified 6-ethylamino-2-picoline.

The best mode contemplated for carrying out the invention is now set forth as follows.

The intermediate 6-acetamido-2-picoline [known: Meyer, Rec. trav. chim. 44, 323 (1925)] was prepared as follows: a mixture containing 420 g. of 6-amino-2-picoline and one liter of acetic anhydride was heated on a steam bath for 1 hour and then evaporated in vacuo on a steam bath to remove the excess acetic anhydride and the acetic acid formed by the reaction. The hot residue was then poured into ice and an excess of ammonium hydroxide was added. The separated precipitate was collected, washed well with water and then recrystallized from benzene to yield 530 g. of 6-acetamido-2-picoline. A solution containing 300 g. of 6-acetamido-2-picoline in about 400 ml. of tetrahydrofuran was added to 1300 ml. of 1 molar diborane ($B_2H_6$) solution in tetrahydrofuran under nitrogen at 0° C. The reaction mixture was stirred for 30 minutes at 0° C., allowed to rise to room temperature and stirred at room temperature for another 30 minutes. The reaction mixture was then slowly brought to reflux and held at reflux for 3 hours. The reaction mixture was chilled and to it was slowly added a solution containing 150 ml. of water and 150 ml. of concentrated hydrochloric acid. To the resulting acidic solution was slowly added potassium hydroxide pellets until the mixture was strongly basic. The alkaline mixture was filtered and the filtrate was concentrated in vacuo. The remaining residue, which contained 6-ethylamino-2-picoline along with some starting material, namely, 6-acetamido-2-picoline, was shaken well with 2,000 ml. of n-hexane. The insoluble 6-acetamido-2-picoline was filtered off and the n-hexane filtrate was washed once with dilute aqueous sodium hydroxide solution and once with brine and then concentrated in vacuo to remove the n-hexane. The remaining residue, consisting primarily of 6-ethylamino-2-picoline, was distilled to yield 90 g. of 6-ethylamino-2-picoline, b.p. 103° C. at 8 mm. The nuclear magnetic resonance spectrum of this compound was determined and found to be consistent with the assigned chemical structure.

I claim:

1. In a process for producing 6-ethylamino-2-picoline by reduction of 6-acetamido-2-picoline, the improvement which comprises reacting 6-acetamido-2-picoline with diborane in an inert non-polar solvent at about 0° to 70° C. to produce 6-ethylamino-2-picoline.

2. In a process for producing 6-ethylamino-2-picoline by reduction of 6-acetamido-2-picoline, the improvement which comprises using a low boiling petroleum solvent to separate the soluble 6-ethylamino-2-picoline from the insoluble 6-acetamido-2-picoline.

3. In a process fo producing 6-ethylamino-2-picoline by reduction of 6-acetamido-2-picoline, the improvement which comprises reacting 6-acetamido-2-picoline with diborane in an inert non-polar solvent at about 0° to 70° C. to produce 6-ethylamino-2-picoline and using a low boiling petroleum solvent to separate the soluble 6-ethylamino-2-picoline from the insoluble 6-acetamido-2-picoline.

4. The process according to claim 1 where the reduction is carried out using tetrahydrofuran as a solvent.

5. The process according to claim 3 where the reduction is carried out using tetrahydrofuran as a solvent.

6. The process according to claim 2 where the low boiling petroleum solvent is n-hexane.

7. The process according to claim 3 where the low boiling petroleum solvent is n-hexane.

8. The process according to claim 3 where the reduction is carried out using tetrahydrofuran as a solvent and the low boiling petroleum solvent is n-hexane.

9. The process for producing 6-ethylamino-2-picoline which comprises reacting 6-acetamido-2-picoline with diborane in an inert non-polar solvent at about 0° to 70° C. to produce 6-ethylamino-2-picoline.

10. The process according to claim 1 which comprises the additional step of using a low boiling petroleum solvent to separate the soluble 6-ethylamino-2-picoline from the insoluble 6-acetamido-2-picoline.

11. The process for producing 6-ethylamino-2picoline which comprises reacting 6-acetamido-2-picoline with diborane in an inert non-polar solvent at about 0° to 70° C. to produce 6-ethylamino-2-picoline and using a low boiling petroleum solvent to separate the soluble 6-ethylamino-2-picoline from the insoluble 6-acetamido-2-picoline.

12. The process according to claim 9 where the inert non-polar solvent is tetrahydrofuran.

13. The process according to claim 10 where the low boiling petroleum solvent is n-hexane.

14. The process according to claim 10 where the inert non-polar solvent is tetrahydrofuran and the low boiling petroleum solvent is n-hexane.

* * * * *

UNITED STATES PATENT AND TRADEMARK OFFICE
CERTIFICATE OF CORRECTION

PATENT NO. : 4,021,437
DATED : May 3, 1977
INVENTOR(S) : Roman R. Lorenz

It is certified that error appears in the above-identified patent and that said Letters Patent are hereby corrected as shown below:

Column 1, line 38, "6-1-ethyl-amino-" should read -- 6-ethylamino- --.

Column 1, line 44, "formamide" should read -- formamidine --.

Column 4, line 36, "-2pico-" should read -- -2-pico- --.

Signed and Sealed this

Twentieth Day of September 1977

[SEAL]

Attest:

RUTH C. MASON
Attesting Officer

LUTRELLE F. PARKER
Acting Commissioner of Patents and Trademarks